(12) United States Patent
Ryoo et al.

(10) Patent No.: US 6,402,716 B1
(45) Date of Patent: Jun. 11, 2002

(54) SYRINGE ASSEMBLY (75) Inventors: Je-Phil Ryoo, Daejeon; Ki-Won Kim, Seoul, both of (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/403,403
(22) PCT Filed: Feb. 12, 1999
(86) PCT No.: PCT/KR99/00076
 § 371 (c)(1),
 (2), (4) Date: Oct. 20, 1999
(87) PCT Pub. No.: WO99/42148
 PCT Pub. Date: Aug. 26, 1999

(30) Foreign Application Priority Data

Feb. 20, 1998 (KR) .............................. 98-5280

(51) Int. Cl.⁷ .............................. A61M 31/00
(52) U.S. Cl. .............................. 604/60
(58) Field of Search .............................. 604/57, 59, 64, 604/93.01, 130–131, 134, 137, 140, 141, 143, 164.01, 164.08, 164.11, 164.12, 181, 187, 192, 272; 606/117–116

(56) References Cited

U.S. PATENT DOCUMENTS 4,820,267 A * 4/1989 Harman
4,846,793 A * 7/1989 Leonard et al.
5,284,479 A * 2/1994 de Jong .............................. 604/60
5,542,920 A * 8/1996 Cherif Cheikh

* cited by examiner

Primary Examiner—Brian L. Casler
Assistant Examiner—LoAn H. Thanh
(74) Attorney, Agent, or Firm—Baker Botts L.L.P.

(57) ABSTRACT

Disclosed is a syringe assembly comprising a hollow barrel having at least one catch therein; a needle part having a protrusion being caught by the catch; an elongated rod which is positioned inside the needle part and fixed on the end portion of the barrel opposite from the distal end of the needle part, the rod having a catch member formed on an end portion thereof opposite the end inserted into the needle part; a pulling member for pulling the needle part to the opposite direction from the distal end of the needle part; and a pressing member mounted to the end of the hollow barrel close to the distal end to of the needle part for releasing the protrusion of the needle part from the catch when external pressure is applied thereupon. The syringe assembly of the present invention further includes a protection member to contain the ejecting elongated rod, a cover member to cover the needle with a small rod formed inside the closed end thereof, the small rod extending at a predetermined distance toward the needle part to keep the same in place and to contain the injection materials therein. The syringe assembly of this invention enables safe and successful injection to large number of animals with minimal required time and skills while minimizing contamination in the injection process.

17 Claims, 15 Drawing Sheets

SYRINGE ASSEMBLY

BACKGROUND OF THE INVENTION (a) Field of the Invention

The present invention relates to a syringe assembly used for animals, and more particularly to a syringe assembly for animals which, upon insertion of a syringe needle manually or by an injection gun, realizes the automatic injection of medication and ejection of the syringe from the animals by means of a self-propelled actuation mechanism.

(b) Description of the Related Art

Manually-operated injection instruments are most commonly used to inject medication into animals. When using such an injection instrument, the animal to be injected must be restrained to facilitate the injection process. That is, the animal must be firmly restrained so that the injection can take place without harm to the animal or the person administering the injection. This is both stressful to the animal and a time-consuming and strenuous process, making the administration of injections to a large number of animals particularly difficult.

In addition to manual injection instruments, various automatic injection instruments are in use including a syringe-type automatic injection instrument and a pressurized automatic injection instrument. However, when using such automatic injection instruments, the experience and skill of the administrator are very important for ensuring the successful and safe injection of the animal. Namely, since these automatic injection instruments instantaneously discharge the medication upon contact with the animal, the use of such instruments requires a high degree of expertise, especially considering the animal often moves during the procedure.

The pressurized automatic injection instruments automatically implant pellets into animals using air or gas pressure. A sensor attached on a head portion of the instrument initiates the injection process when put in contact with the animal. Such pellets, which are cylindrical or ovoid compressed masses of protein as an active ingredient, such as animal growth hormones mixed with pharmaceutical excipients, have been proven to display much better medicinal effects, durability and stability for animals than medication injected in a liquid form. However, it is a particularly difficult task to inject the hard pellets since the injection needs to be conducted instantaneously at an exact location on the body of a moving animal.

Another type of injection instrument used is a blowgun-type injection device. A syringe assembly- including a needle, a medication holder and a gas charge- is placed in a blowgun and shot toward the animal by the user aiming the blowgun and blowing on an end of the same in a direction toward the animal. Accordingly, the syringe assembly is directed to a desired location on the animal and gas is discharged upon impact of the needle such that the medicine in the medication holder is injected in the animal. However, a problem with such a device is that the syringe assembly is left remaining in the body of the animal after the injection procedure. Also, it is possible to harm the animal if the syringe assembly is directed on a part of the body which would injure the animal.

Accordingly, there is a need to develop an injection instrument for animals, especially for the injection of hard pellets, which requires little contact with the animal to be injected, operates instantaneously on exact locations of the animal body, requires minimal experience and skill to safely and successfully administer injections, reduces the chance of unsuccessful injections caused by a reflex action of the animal (resulting in the loss of part or all of the medication), and prevents the contamination of the needle.

SUMMARY OF THE INVENTION

The present invention has been made in an effort to solve the problems of the prior art and fulfill the above needs.

It is an objective of the present invention to provide a syringe assembly having a disposable injector incorporating a self-propelled actuation mechanism which enables self-ejection from the body after injection of medication is completed. In particular, it is an objective of the present invention to provide a syringe assembly which obviates the need to restrain animals.

It is another objective of the present invention to provide a syringe assembly which reduces the amount of manpower required and the injection time.

It is yet another objective of the present invention to provide a syringe assembly which enables efficient administration of injections such that injecting a large number of animals is easy.

It is still yet another objective of the present invention to provide a syringe assembly which requires minimal experience and skill to safely and successfully administer injections.

It is still yet another objective of the present invention to provide a syringe assembly which is disposal, thereby preventing needle contamination.

To achieve the above objectives, the present invention provides a syringe assembly including a hollow barrel having at least one catch therein; a needle part having a needle and a protrusion being caught by the catch; an elongated rod which is positioned inside the needle part and fixed on the end portion of the barrel opposite from a distal end of the needle, the rod having a catch member formed on an end portion thereof opposite the end inserted into the needle; a pulling member for pulling the needle part and the elongated rod to the opposite direction from the distal end of the needle; and a pressing member mounted to an end of the hollow barrel close to the distal end of the needle for releasing the protrusion of the needle part from the catch when external pressure is applied thereupon. The syringe assembly of the present invention further includes a protection member to seal the barrel and contain the ejecting elongated rod, a cover member to cover the needle with a small rod formed inside a closed end thereof, the small rod extending at a predetermined distance toward the needle to keep the same in place and to contain injection materials therein.

BRIEF DESCRIPTION OF THE DRAWINGS

A more complete appreciation of the invention will be readily apparent as the same becomes better understood by reference to the following detailed description when considered in conjunction with the accompanying drawings, wherein.

DETAILED DESCRIPTION OF THE INVENTION

Reference will now be made in detail to the preferred embodiments of the present invention, examples of which are illustrated in the accompanying drawings.

Figure 1:
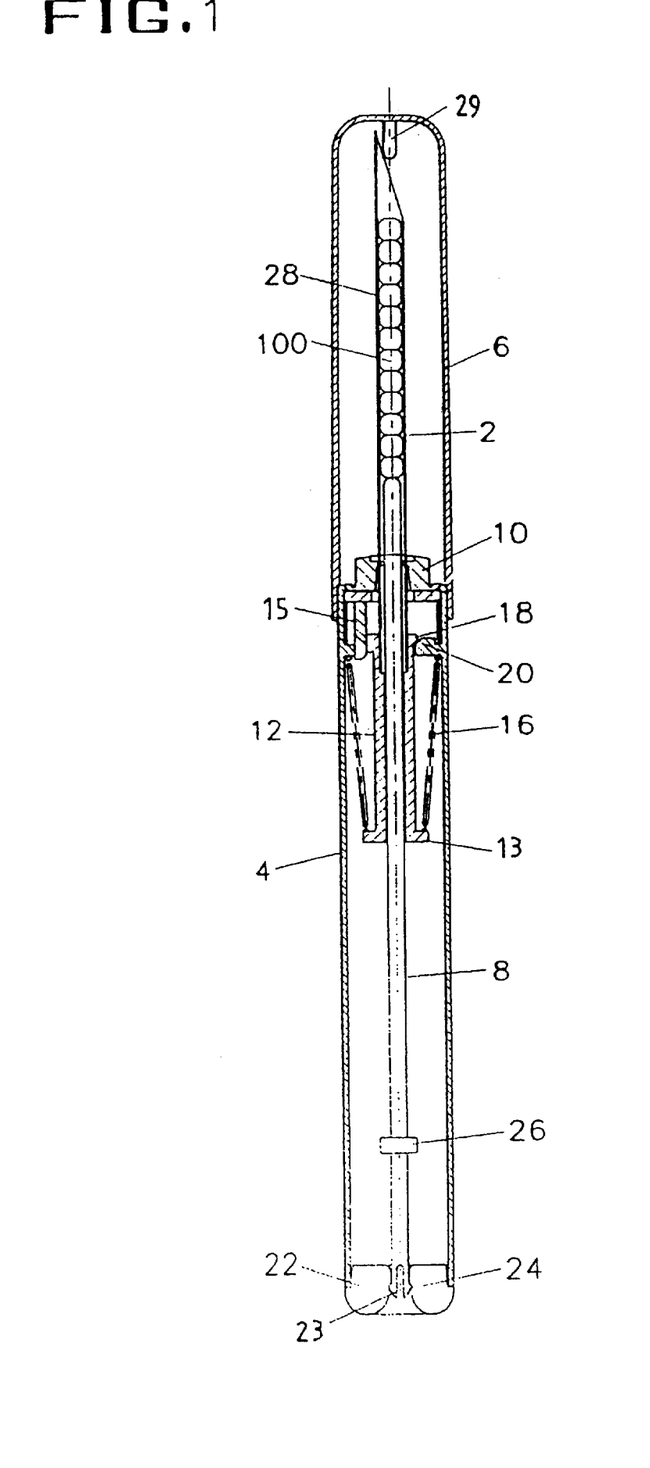
FIG. 1 is a sectional view of a syringe assembly according to a first preferred embodiment of the present invention.

FIG.1 shows a sectional view of a syringe assembly according to a first preferred embodiment of the present invention. An exterior of the syringe assembly is defined by a cover member 6 and a hollow barrel 4, the cover member 6 being detachably connected to the hollow barrel 4. The cover member 6 covers most of a needle 2, with one end of the needle 2 extending into the hollow barrel 4. A small rod 29 is formed inside a closed end of the cover member 6. The small rod 29 extends at a predetermined distance toward the needle 2 to keep the same in place. One end of the hollow needle 2, which retains an injection material 100, is fixedly mounted on a needle holder 12. The needle and the needle holder comprises a needle part of this invention. The needle holder 12 has a protrusion 18, at an end securing the needle 2, extending in a direction toward the hollow barrel 4, and a hollow plate 13 at its opposite end.

The needle 2 slides along an outer surface of an elongated rod 8, one end of which is inserted into the needle 2 for injecting the material 100. The elongated rod 8, which can be detached from the barrel 4, extends the length of the barrel 4 and has a catch member 26 formed on an end portion opposite that of the end inserted into the needle 2, and a small protrusion 24 is formed on this end of the elongated rod 8. The hollow plate 13 of the needle holder 12 contacts and pushes the catch member 26 of the elongated rod 8 when the needle holder 12 together with the attached needle 2, moves in this direction 26. Subsequently, the elongated rod 8 on which the catch member 26 is formed protrudes out from the end of the barrel 4.

A hollow pressing member to actuate the withdrawal of the needle 2, is mounted to the end of the barrel 4 connected to the cover member 6, the hollow pressing member 10 surrounding the needle 2. The hollow pressing member 10 has a small hollow bar 15 extending therefrom in a direction toward the needle holder 12. When the needle 2 is not actuated, the protrusion 18 of the needle holder 12 is held fast between the hollow bar 15 and a catch 20 formed extending from an inner wall of the barrel 4 in a direction toward the needle holder 12. The catch 20 corresponds to the position of the protrusion 18 of the needle holder 12 when the needle 2 is in a non-actuated state as shown in FIG. 1. Further, an pulling member 16 such as a spring is provided surrounding the needle holder 12, and is interposed between the catch 20 and the hollow plate 13 of the needle holder 12. The pulling member 16 is in a compressed state in FIG. 1.

Provided on an end of the barrel 4 opposite that connected to the cover member 6 is a fixing member 22. The fixing member 22 is hollow in its center and surrounds the end of the elongated rod 8 on which the protrusion 24 is formed. A groove 23 in the center of the fixing member 22 is to be fitted with the protrusion 24 of the elongated rod 8. The protrusion 24 detaches from the groove 23 of the fixing member 22 when the elongated rod 8 is projected out this end of the barrel 4.

The operation of the syringe assembly according to the first preferred embodiment of the present invention will now be described.

First, the cover member 6 is removed by user such that the needle 2 is exposed. After the needle 2 is stuck into the body of an animal, the pressing member 10 is pressed by contact with the body and lowers to the direction opposite from the distal end of the needle. Accordingly, the protrusion 18 of the needle holder 12 is disengaged from the catch 20 of the barrel 4 and the pulling member 16 expands from its compressed state, thereby moving the needle holder 12 in a direction toward the catch member 26 of the elongated rod 8. With the continued exertion of the biasing force of the pulling member 16, the elongated rod 8 is also moved to protrude out of the barrel.

To prevent the loss of injection material, it is preferable that a sharp end of the needle 2 be covered with a membrane, or an oil film is coated on an inner wall 28 of the needle 2. Also, it is preferable that the injection material is a hard, semi-liquid, or liquid composition including substances useful for the body. More preferably, the substances are proteins, particularly animal growth hormones, and most preferably the substances are growth hormones for cows or pigs manufactured by a genetic engineering process.

The administration of the injection material using the syringe assembly according to the first embodiment of the present invention will be described in more detail.

Figure 2:
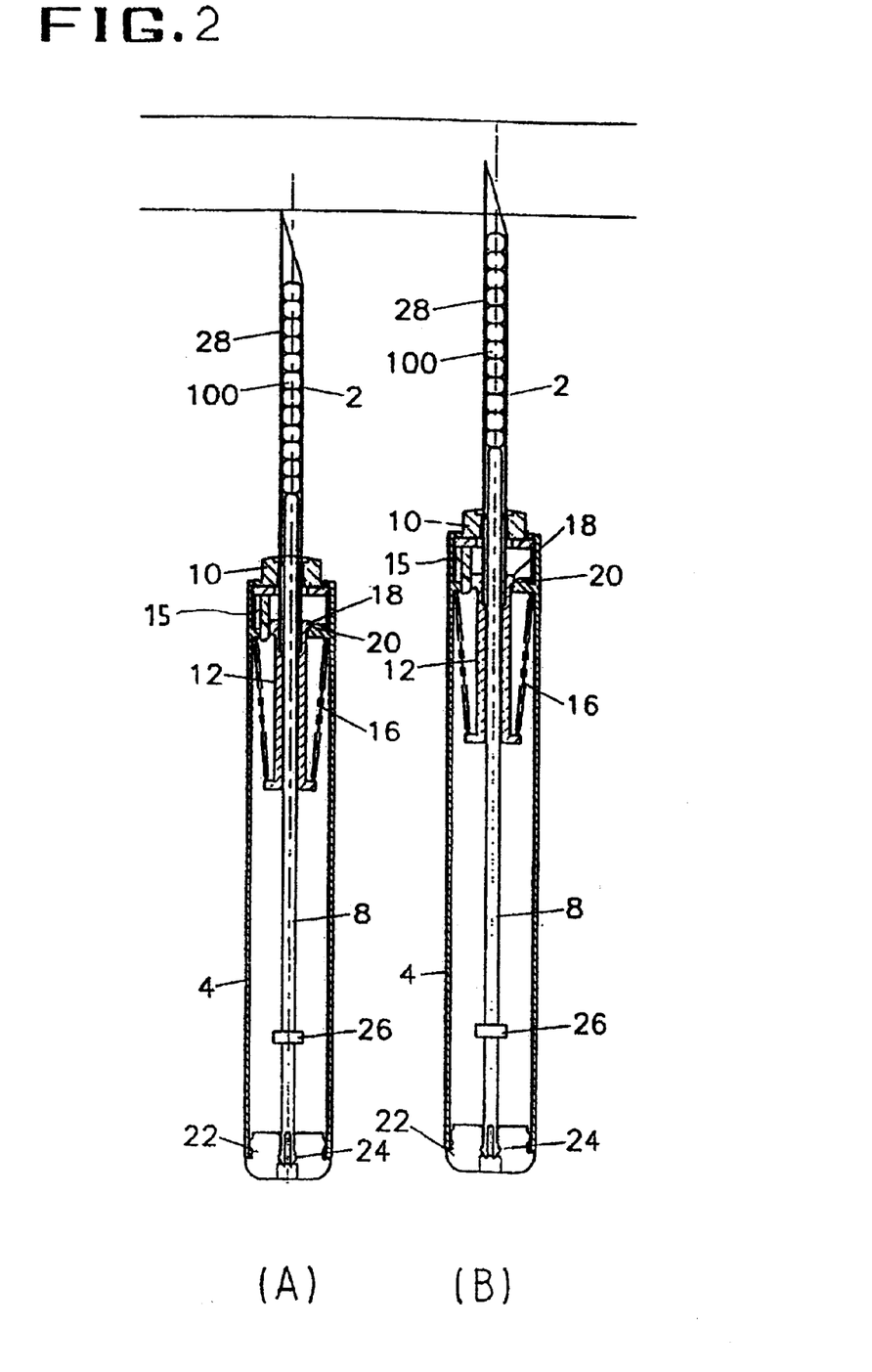
FIG. 2 shows sectional views of the syringe assembly of FIG. 1 used to describe a state where a needle makes contact with the body of an animal.

After removal of the cover member 6 by the user, the injection instrument is either shot from an injection gun or manually operated to inject a substance into an animal at a predetermined location thereon. The needle 2 of the instrument advances into the body as shown in FIG. 2(A) and FIG. 2(B). The needle 2 continues its movement into the body of the animal until the pressing member 10 contacts the body as shown in FIG. 3.

Figure 3:
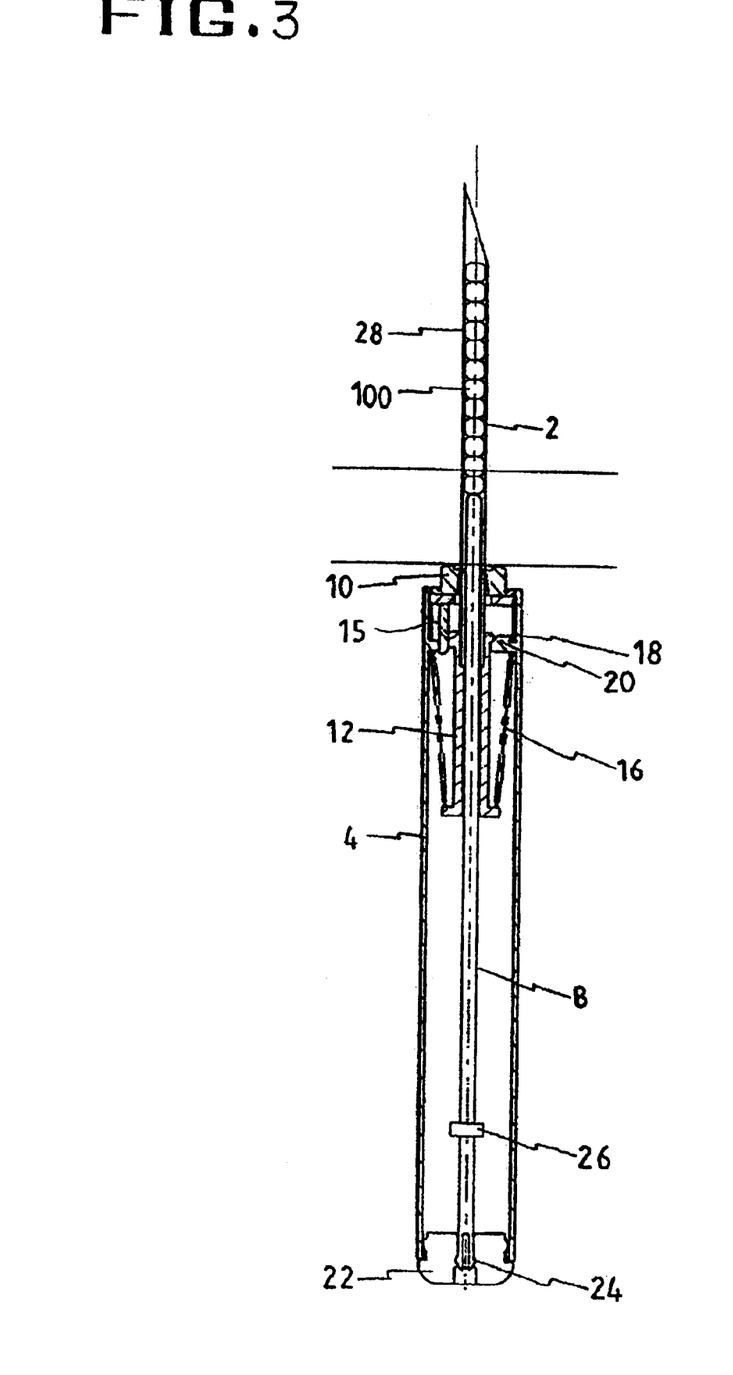
FIG. 3 is a sectional view of the syringe assembly of FIG. 1 in a state where a pressing member of the syringe assembly is in contact with the body of an animal.
Figure 4:
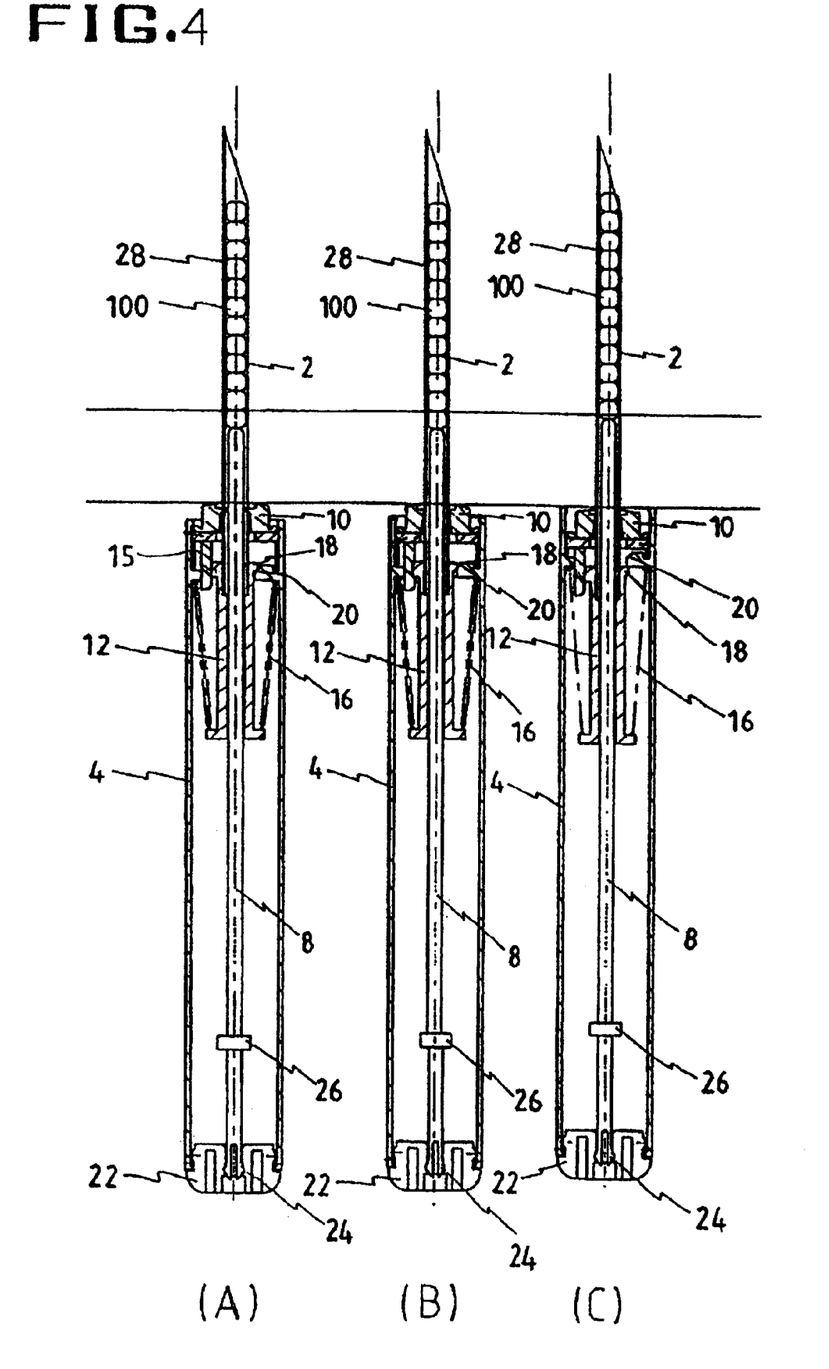
FIG. 4 shows sectional views of the syringe assembly of FIG. 1 in a state where an pulling member is actuated by pressure of the pressing member.
Figure 5:
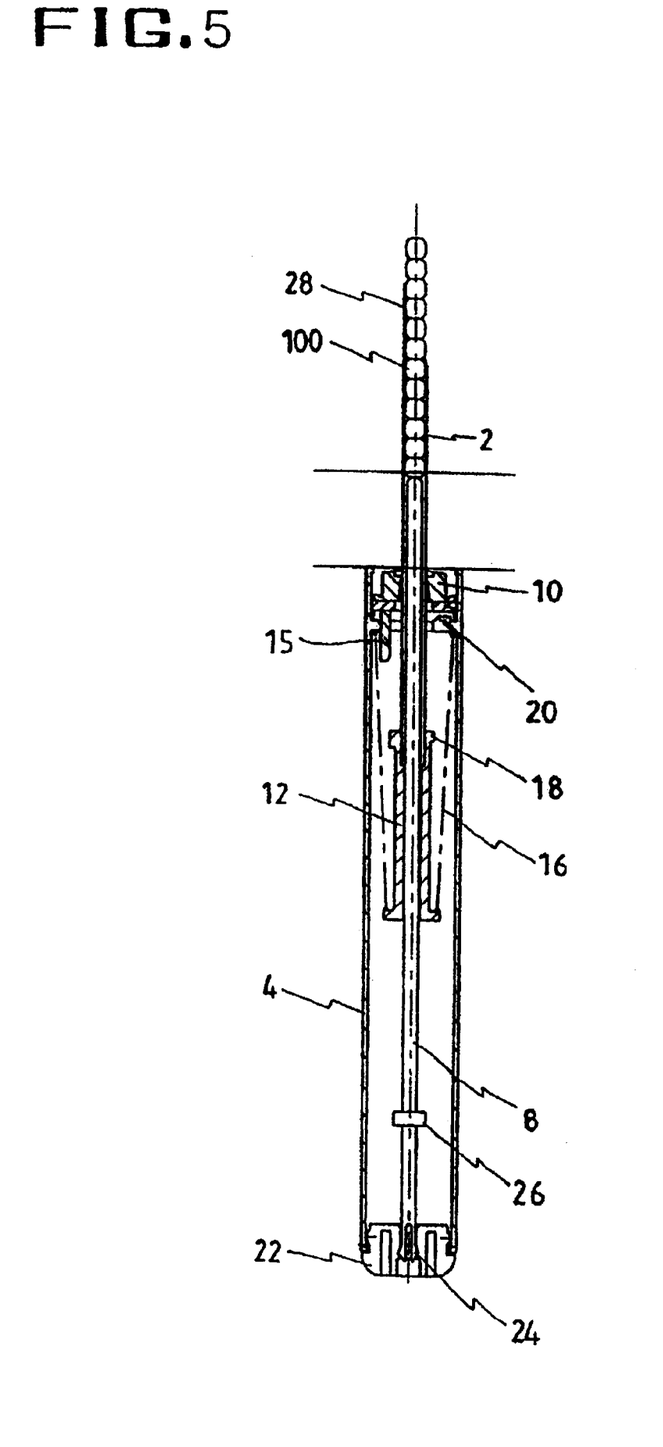
FIG. 5 is a sectional view of the syringe assembly of FIG. 1 in a state where a needle begins to retreat upon release of the pulling member from its compressed state.
Figure 9:
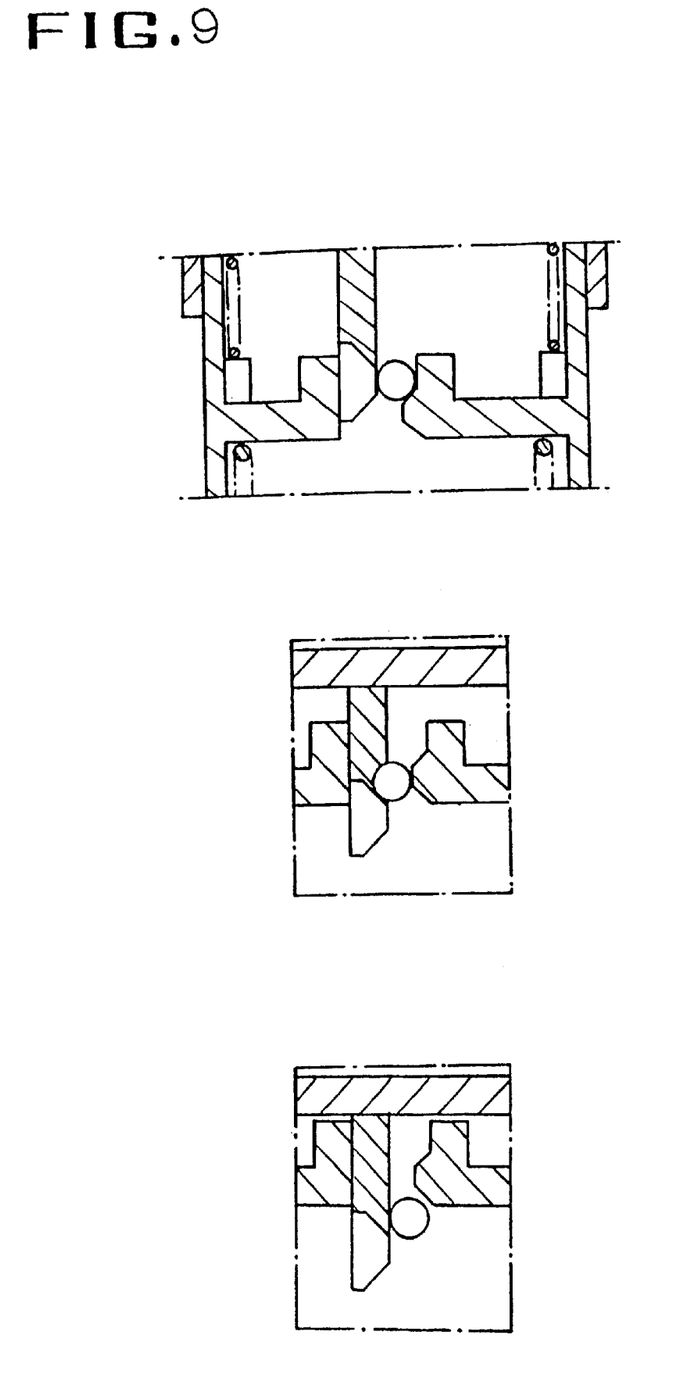
FIG. 9 is a partial sectional view of the syringe assembly of FIG. 1 showing how a protrusion of the needle holder is separated from a catch provided on the wall of the syringe barrel.

Next, referring to FIGS. 4(A), 4(B) and 4(C), in a state where the needle 2 is fully inserted and the pressing member 10 is in contact with the body of the animal as shown in FIG. 3, with continued movement of the syringe assembly toward the animal the pressing member 10 is pressed such that the same with the extended bar 15 having a hole therethrough starts to lower. Accordingly, the protrusion 18 slides into the hole of the bar 15, bringing the whole needle slightly to the direction of the bar 15 and in its process, the protrusion 18 of the needle holder 12 is released from the catch 20 as shown in FIG. 4(C). The separating of the protrusion 18 from the catch 20 is also shown in FIG. 9. In FIG. 9, the needle holder attached on the needle is indicated as a circle in the middle. This releases the pulling member 16 from its compressed state such that the needle holder 12 and the needle 2 are moved in a direction toward the catch member 26 of the elongated rod 8 as shown in FIG. 5.

Figure 6:
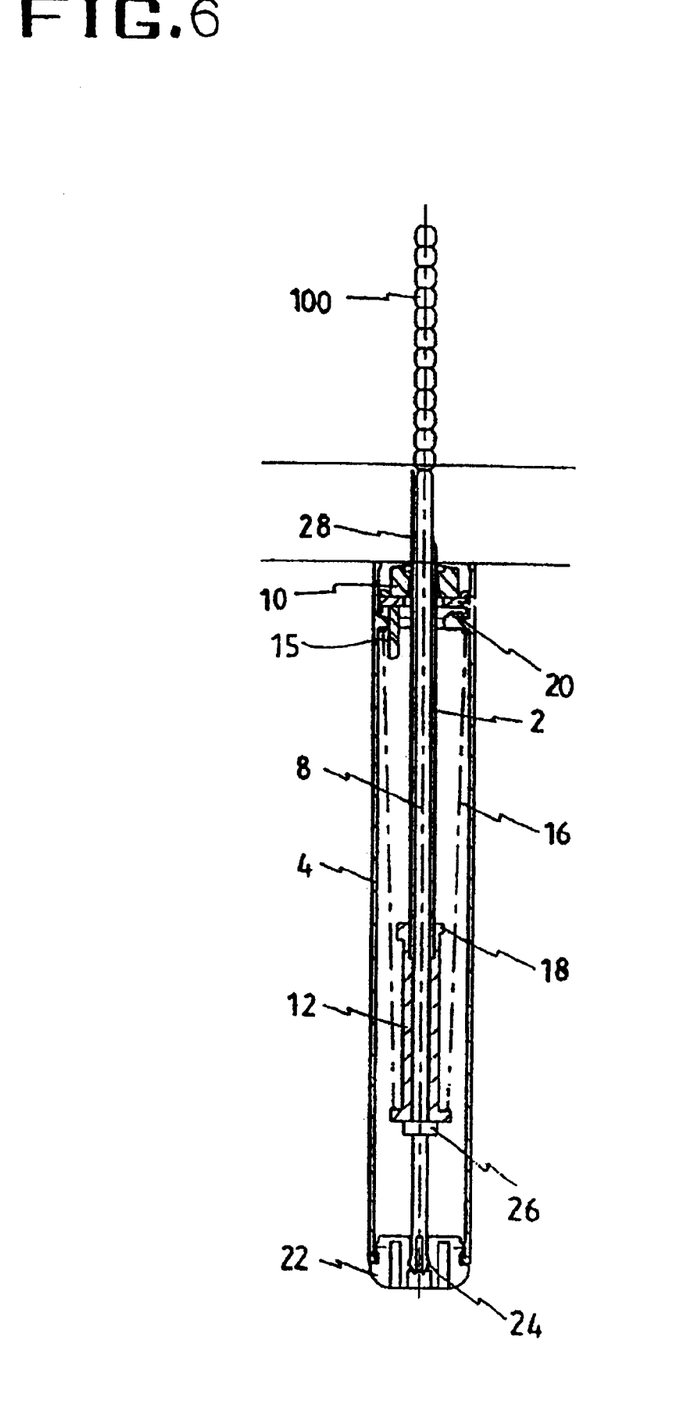
FIG. 6 is a sectional view of the syringe assembly of FIG. 1 in a state where a needle holder drawn by the pulling member arrives at a position of a protrusion member of an elongated rod.
Figure 7:
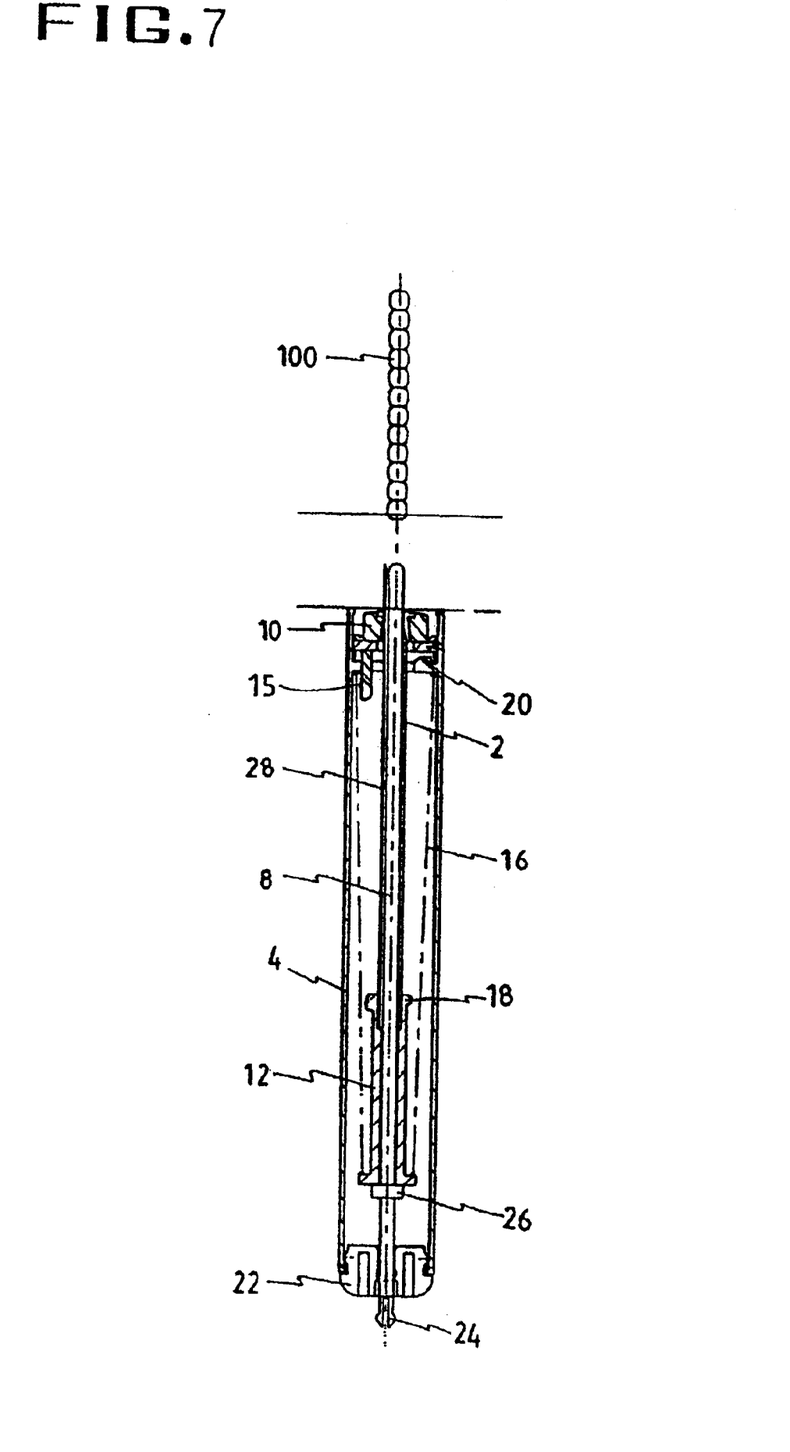
FIG. 7 is a sectional view of the syringe assembly of FIG. 1 in a state where the elongated rod is actuated to move to a rear of a syringe barrel.

Referring now to FIG. 6 and FIG. 7, the needle 2 and the needle holder 12 continue to move in this direction away from the body of the animal until the hollow plate 13 of the needle holder 12 contacts the catch member 26 of the elongated rod 8. In this state, the injection material 100 is fully injected into the body of the animal. With the continued exertion of the biasing force of the pulling member 16, the needle holder 12 continues to push against the catch member 26 of the elongated rod 8, thereby further moving these elements in the same direction.

Figure 8:
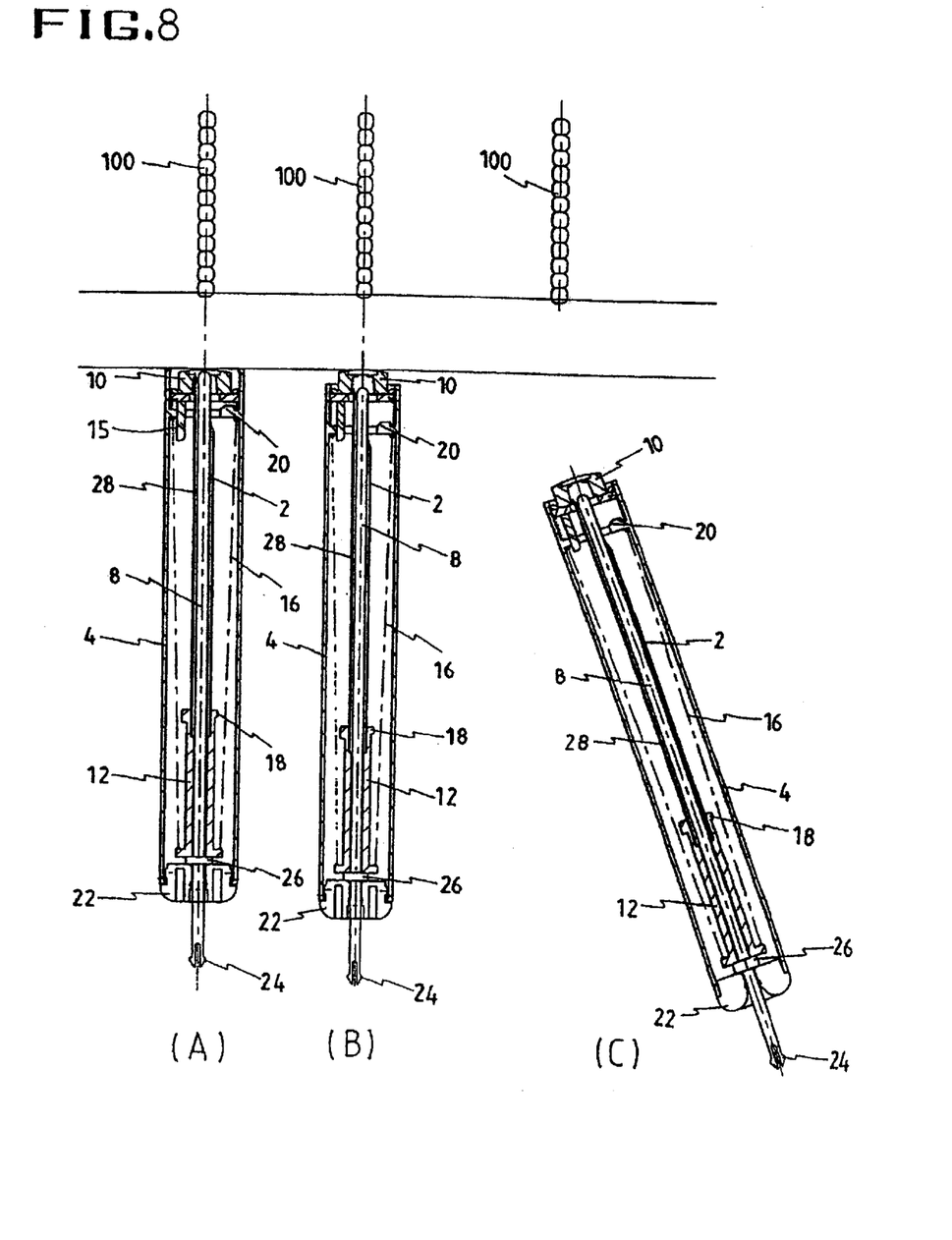
FIG. 8 shows sectional views of the syringe assembly of FIG. 1 in a state where the syringe barrel is separated from the animal body.

As shown in FIGS. 8(A), 8(B) and 8(C), the needle 2 continues to retreat out of the body of the animal, completing the injection process. In this process, the protrusion 24 of the elongated rod 8 detaches from the groove 23 of the fixing member 22.

Figure 10:
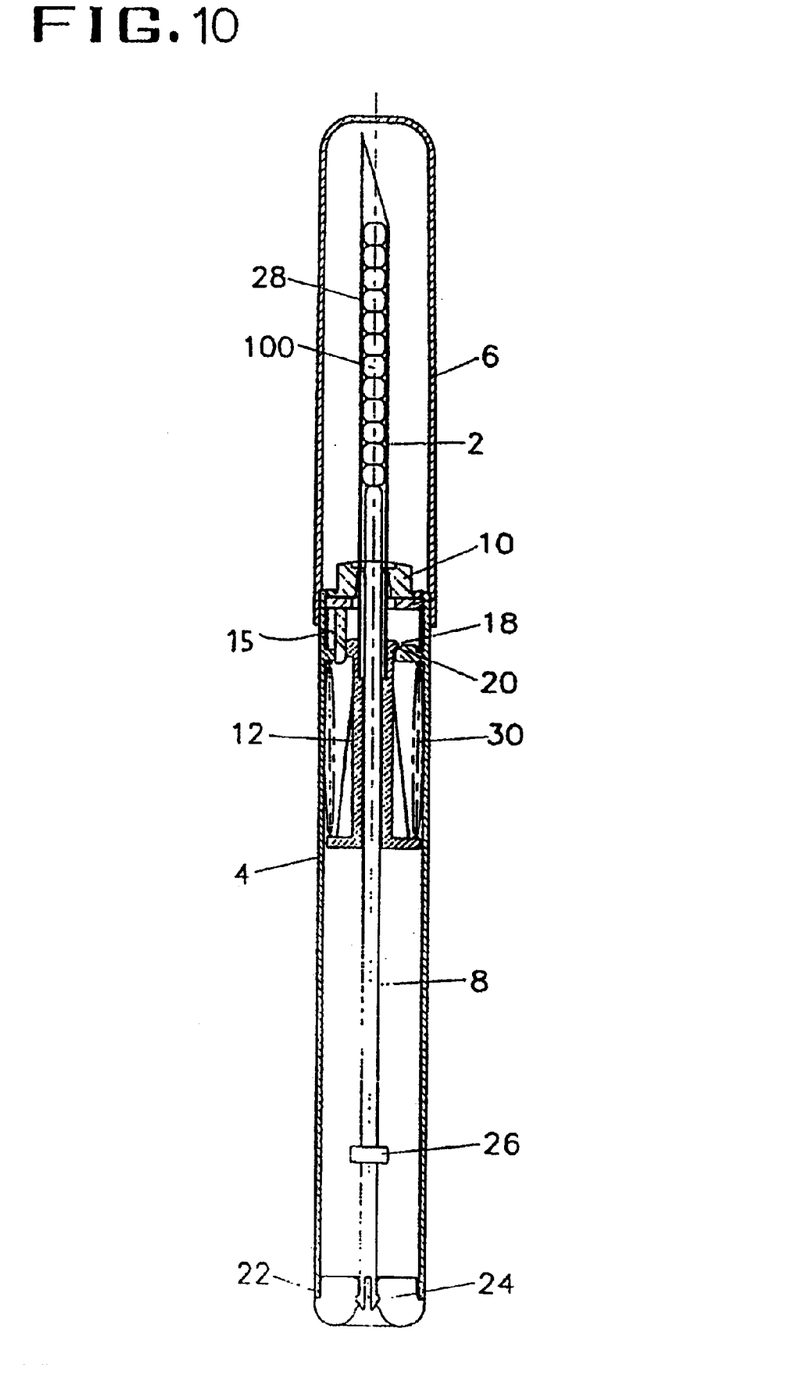
FIG. 10 is a sectional view of a syringe assembly according to a second preferred embodiment of the present invention.

FIG. 10 shows a sectional view of a syringe assembly according to a second preferred embodiment of the present invention. In the drawing, like reference numerals will be used for elements identical in structure and operation to that disclosed in the syringe assembly of the first preferred embodiment.

In the syringe assembly of the second embodiment, the pulling member 16 of the first preferred embodiment is substituted by a gas bag 30. Gas emitted from the gas bag 30 serves to actuate the withdrawal of the needle 2 from the body of the animal. That is, when pressure is applied on the pressing member 10, as a result of contact with the body of an animal, the protrusion 18 of the needle holder 12 is released from the catch 20 as in the first embodiment. As a result, the gas bag 30 explodes, generating the force needed to push the needle 2 and the elongated rod 8 in a direction away from the body of the animal as in the first preferred embodiment of the present invention.

Figure 11:
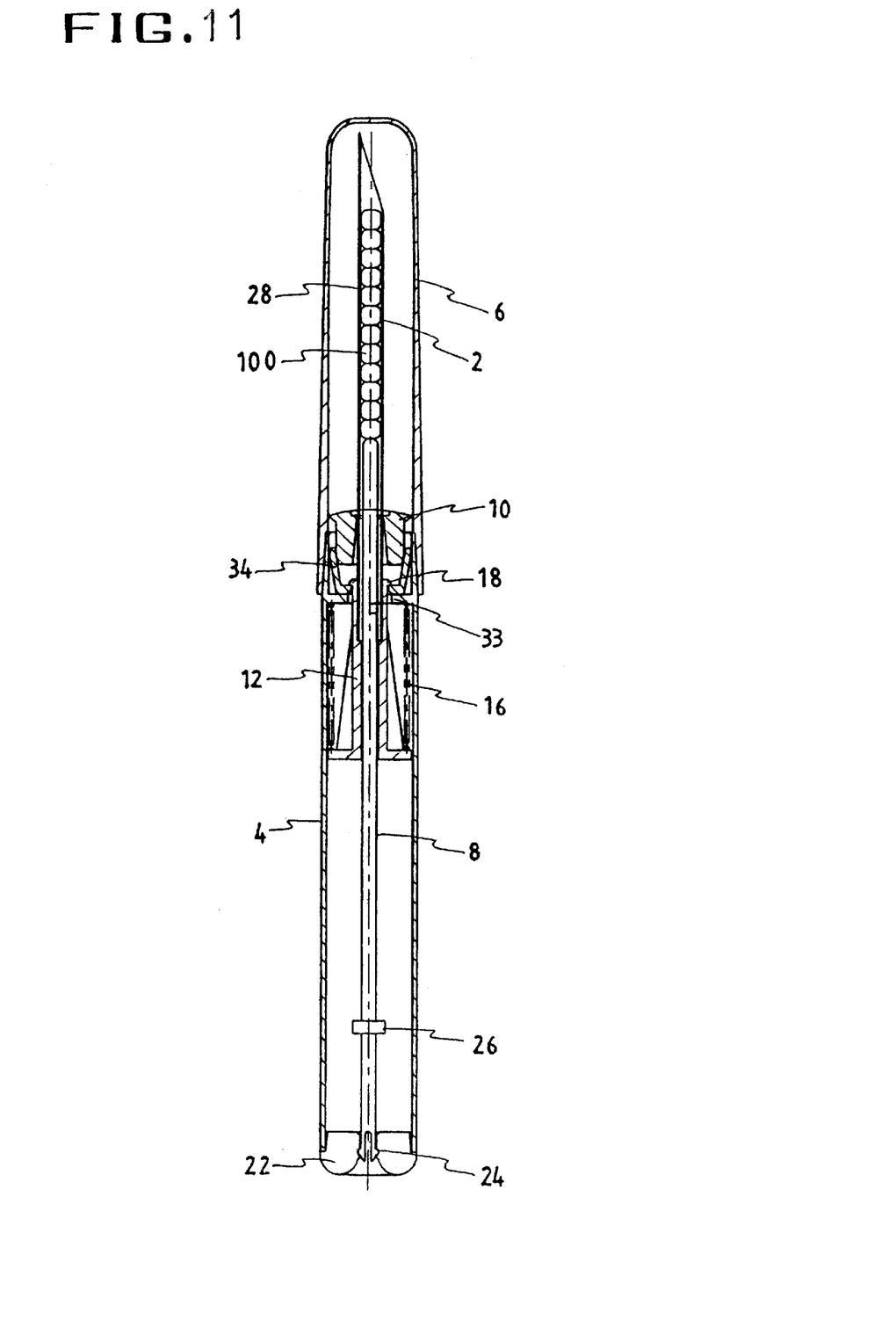
FIG. 11 is a sectional view of a syringe assembly according to a third preferred embodiment of the present invention.

FIG. 11 shows a sectional view of a syringe assembly according to a third preferred embodiment of the present invention. In the drawing, like reference numerals will be used for elements identical in structure and operation to that disclosed in the syringe assembly of the first preferred embodiment.

In the syringe assembly of the third preferred embodiment, the actuation mechanism is carried out by the needle holder 12 having a protrusion 18 on an end A corresponding to where the needle 2 is mounted thereto, the pressing member 10, a pulling member 16, and an elastic catch 34. The elastic catch 34 is provided between the pressing member 10 and a flange 33 formed in the barrel 4. One end of the elastic catch 34 is inserted between the pressing member 10 and an inner wall of the barrel, while the other end of the elastic catch 34 rests on the flange 33 of the barrel 4, with the protrusion 18 of the needle holder 12 caught on the elastic catch 34. As shown in the drawing, a space is formed between the inner wall of the barrel 4 and the elastic catch 34 when the same is in a state of rest. The elastic catch 34 is able to be pushed into this space to be flush against the wall. The flange 33 is structured such that it does not catch on the protrusion 18 of the needle holder 12 when the same is released.

As the pressing member 10 is pressed by contact with the body of an animal, the catch 34 is pushed back toward the inner wall of the barrel 4, thus, releasing the protrusion 18 of the needle holder 12. Accordingly, the needle holder 12 moves in a direction away from the animal by the release of the pulling member 16 from its compressed state. Subsequently, the remaining elements of the syringe assembly operate identically as in the first embodiment to inject the injection material 100 into the animal.

Figure 12:
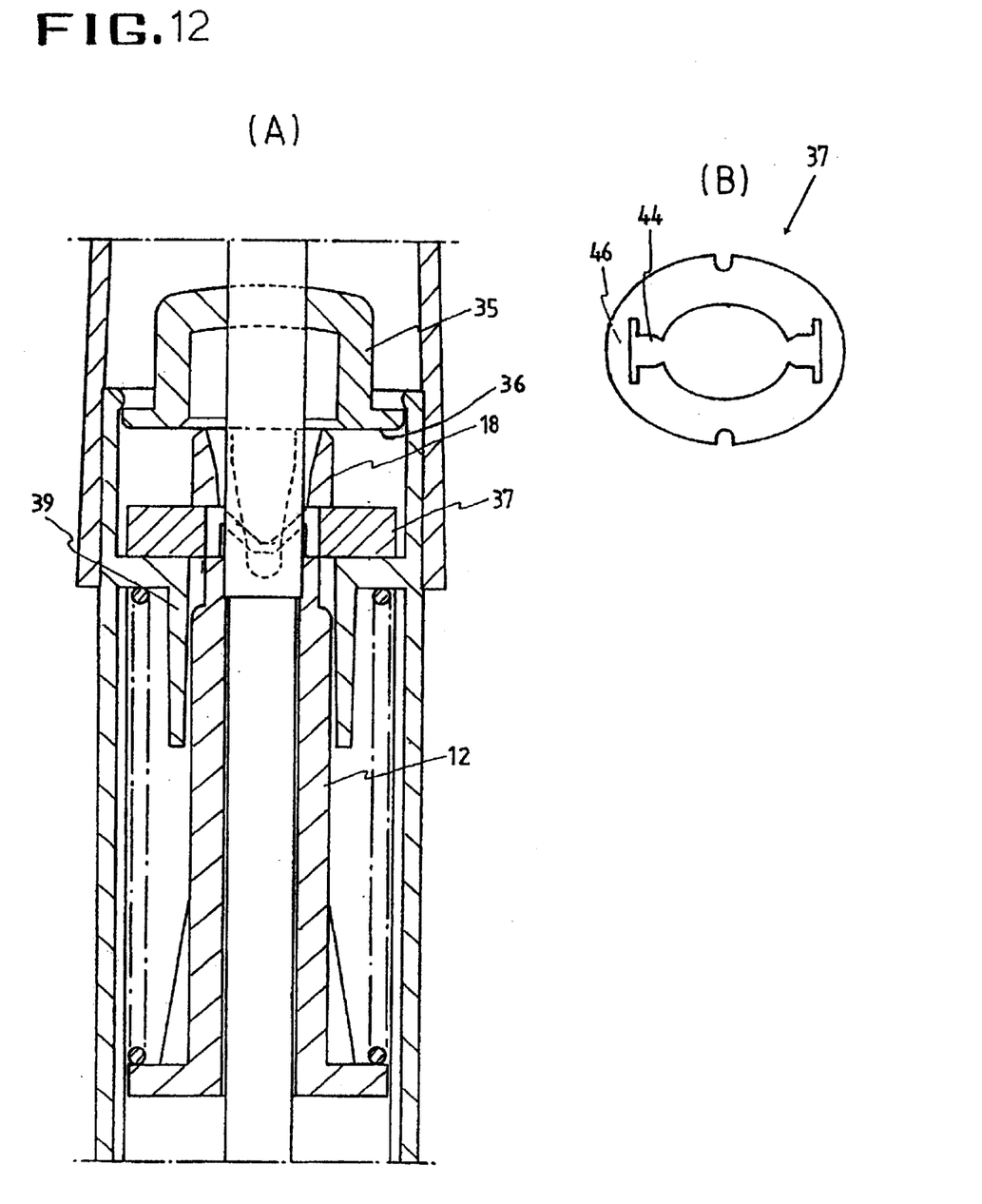
FIG. 12A is a partial sectional view of a syringe assembly according to a fourth preferred embodiment of the present invention.
FIG. 12B is a perspective view of a pressing plate shown in FIG. 12A.

FIG. 12 (A) and FIG. 12 (B) show partial sectional views of a syringe assembly according to a fourth embodiment of the present invention. In the drawing, like reference numerals will be used for elements identical in structure and operation to that disclosed in the syringe assembly of the first preferred embodiment.

The syringe assembly of the fourth embodiment includes a thimble-shaped hollow pressing member 35 which has a hole in a center thereof and two legs 36 extending toward the inner surface of the barrel 4 on an end opposite where the hole is formed. The two legs 36 have large diameter in its end close to the pressing member 35, and small diameter at the opposite end. A guide extension 39 is formed protruding inward from the inner surface of the barrel 4 then extending in a direction away from the pressing member 35. A pressing plate 37 is mounted on the guide extension 39. A protrusion 18 of the needle holder 12 catches on the pressing plate 37 to prevent the needle holder 12 from being released.

The pressing plate 37 has a roughly oval-shaped aperture in a center thereof, the aperture being extended to form receiving holes 44 for the two legs of the pressing member 35. The aperture can be widened when the two legs of the pressing member 35 are fully inserted into the receiving holes 44. The expansion of the inner circle of the donut-shaped pressing plate outwardly results in the release of the protrusion around the top of the needle holder from its hold. Thereafter, the syringe assembly operates identically as that described with the first embodiment to inject the injection material 100 into an animal.

Figure 13:
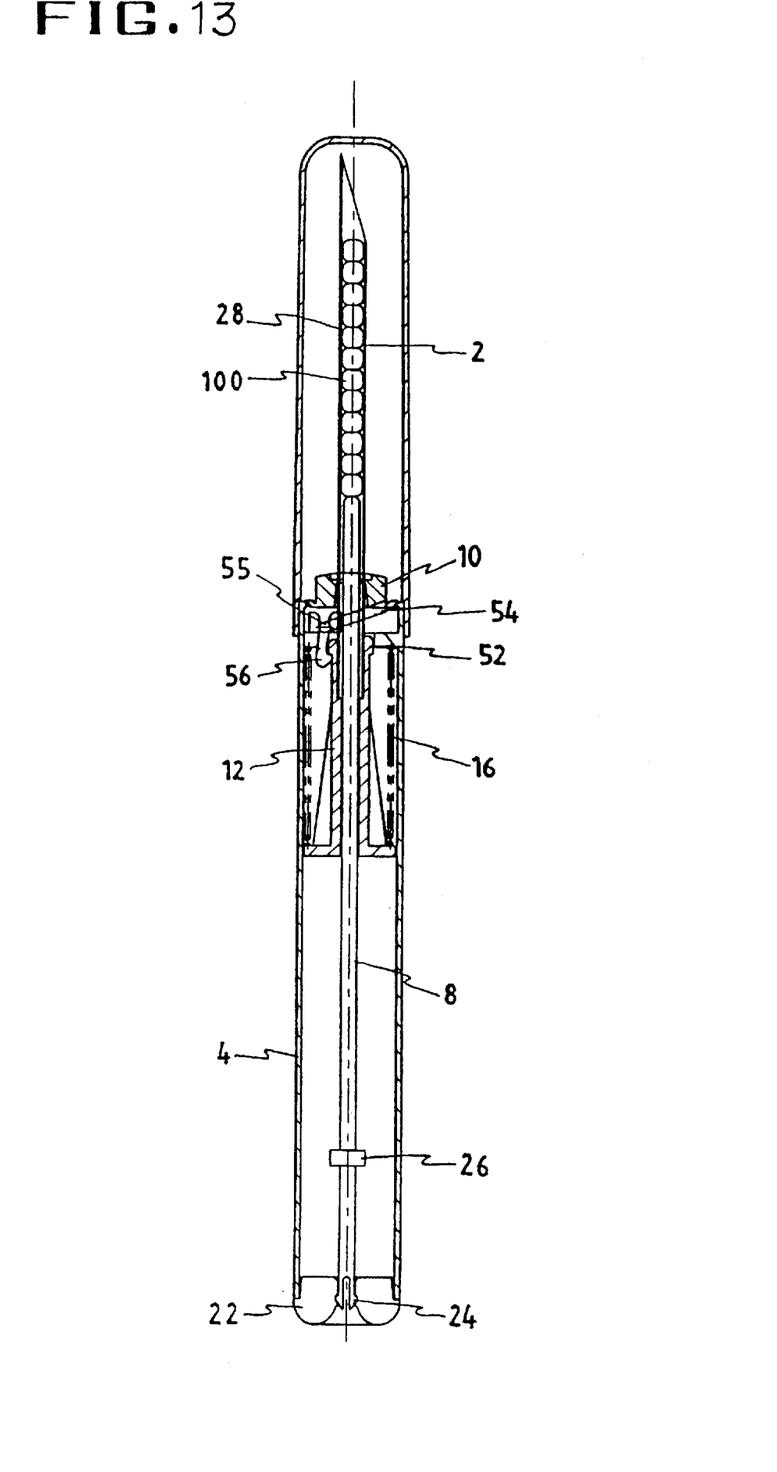
FIG. 13 is a sectional view of a syringe assembly according to a fifth preferred embodiment of the present invention.

FIG. 13 shows a syringe assembly according to a fifth embodiment of the present invention. In the drawing, like reference numerals will be used for elements identical in structure and operation to that disclosed in the syringe assembly of the first preferred embodiment.

In the syringe assembly of the fifth embodiment, the actuation mechanism is initiated by the pressing member 10, and a pressing lever 54 connected with the barrel 4 at one end and pushed by the pressing member 10. The pressing lever 54 has a hole in a center thereof through which the needle 2 passes. A rotating member 55 is formed on one end of the pressing lever 54 and a catch 56 is also connected to the rotating member 55. With this structure, when the pressing lever 54 is pushed by the pressing member 10, the catch 56 moves in a direction away from the needle holder 12, thereby being released from the same. Accordingly, the syringe assembly operates identically as that described with the first embodiment to inject the injection material 100 into an animal.

Figure 14:
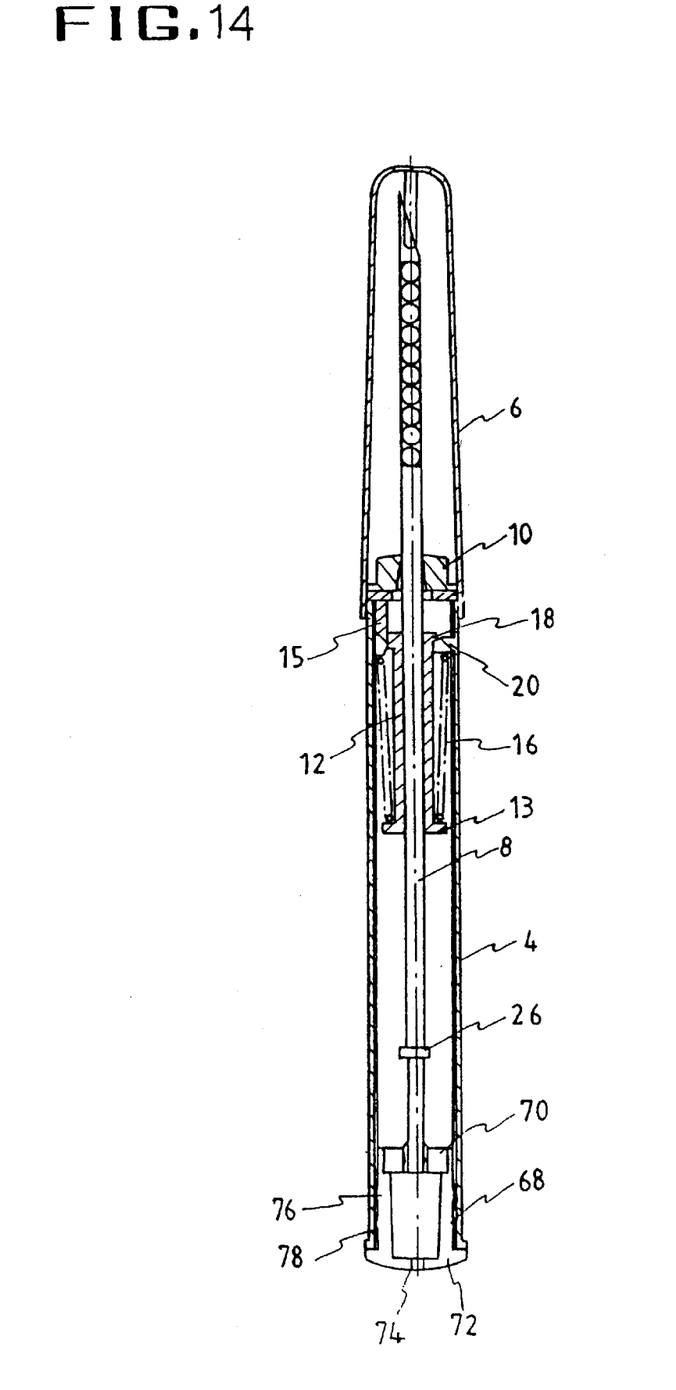
FIG. 14 is a sectional view of a syringe assembly according to a sixth preferred embodiment of the present invention.
Figure 15:
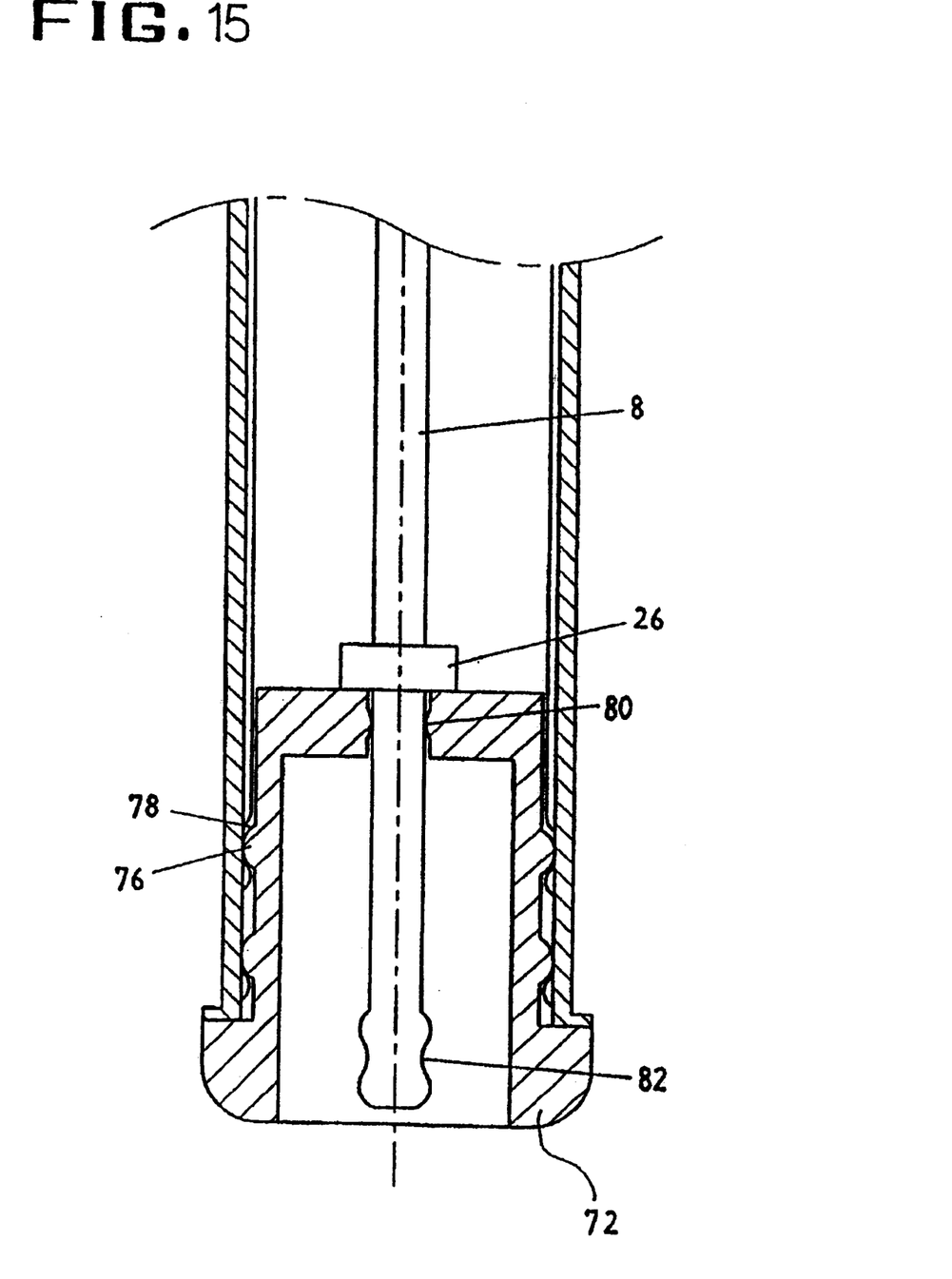
FIG. 15 is a partial sectional view of the syringe assembly shown in FIG. 14.

FIG. 14 and FIG. 15 respectively show a sectional view and a partial sectional view of a syringe assembly according to a seventh embodiment of the present invention. In the drawing, like reference numerals will be used for elements identical in structure and operation to that disclosed in the syringe assembly of the first preferred embodiment.

In the syringe assembly of the seventh embodiment, a structure of the end of the barrel 4 opposite where the same is connected to the cover member 6 is altered from the other embodiments. That is, this end of the barrel 4 is sealed by a protection member 72. The protection member 72 is a hollow cylinder structure having an aperture 74 formed on one end and a ridge 70 formed on an inserting end, the catch member 26 of the elongated rod 8 contacting the ridge 70 during the actuation of the syringe assembly.

A plurality of rings 76 are formed on a circumference of the protection member 72, and a plurality of grooves 78 are formed in an inside circumference of the barrel 4, the grooves 78 corresponding to the rings 76. With the formation of the rings 76 and the grooves 78, the protection member 72 is securely maintained in the barrel 4. Further, as shown in FIG. 15, a protruding band 80 is formed on an inside circumference of the ridge 70 of the protection member 72. The band 80 is inserted in a channel 82 formed on a circumference of the end of the elongated rod 8 when the same is positioned in this location. This structure is provided to contain the ejecting elongated rod 8 inside the barrel 4 such that any possible injuries which might be caused by the powerfully ejecting elongated rod is prevented. Other embodiments of the invention will be apparent to the skilled in the art from consideration of the specification and practice of the invention disclosed herein. It is intended that the specification and examples be considered as exemplary only, with the true scope and spirit of the invention being indicated by the following claims.

What is claimed is:

1. A syringe assembly comprising:

a hollow barrel having at least one catch therein;

a needle part comprising a needle for holding medicine and a needle holder secured to the needle and having a protrusion on its outer surface;

an elongated rod which is positioned inside the needle part and fixed on an end portion of the barrel opposite from a distal end of the needle part;

a pulling member for pulling the needle part to a direction opposite from the distal end of the needle part; and a pressing member mounted to an end of the hollow barrel close to the distal end of the needle part for releasing the protrusion from the catch of the barrel when the pressing member is pressed by contacting the body of an animal at the site of injection.

2. A syringe assembly according to claim 1, wherein the needle is adapted to hold medicine of a hard, semi-liquid or liquid composition.

3. A syringe assembly according to claim 2, wherein the medicine is an animal growth hormone.

4. A syringe assembly according to claim 3, wherein the animal growth hormone is a growth hormone for cows or pigs manufactured by genetic engineering process.

5. A syringe assembly according to claim 2, wherein the medicine is a protein.

6. A syringe assembly according to claim 1, wherein the needle holder further comprises a plate on its bottom for supporting the pulling member.

7. A syringe assembly according to claim 3, wherein the pulling member is positioned between the plate of the needle holder and the catch of the barrel.

8. A syringe assembly according to claim 1, wherein the elongated rod has a catch member formed on an end portion thereof opposite the end inserted into the needle, the catch member enabling the pulling of the elongated rod by the pulling member to the opposite direction from the distal end of the needle.

9. A syringe assembly according to claim 8, wherein a protection member is provided at the end of the barrel opposite from the distal end of the needle to contain the elongated rod.

10. A syringe assembly according to claim 1, wherein a cover member is included to cover the needle .

11. A syringe assembly according to claim 10, wherein a small rod is formed inside a closed end of the cover member, the small rod extending at a predetermined distance toward the needle to keep the same in place and to contain medicine therein.

12. A syringe assembly according to claim 1, wherein the pressing member has a small hollow bar extending therefrom, the end of which not connected with the pressing member is positioned between the protrusion and the catch, and which has a hole in the center to enable the disengagement of the protrusion from the catch.

13. A syringe assembly according to claim 1, wherein the pulling member is a spring.

14. A syringe assembly according to claim 1, wherein the pulling member is a gas bag.

15. A syringe assembly according to claim 1, wherein the catch is provided between the pressing member and a flange formed in the barrel having a hole in the center, one end of the catch inserted between the pressing member and an inner wall of the barrel, the other end catching the protrusion of the needle part and resting on the flange, the catch being capable of disengaging the protrusion when the same is pushed against the wall into a space formed between the inner wall of the barrel and the catch.

16. A syringe assembly according to claim 1, wherein the pressing member has a plurality of legs extending therefrom, and the catch made of a resilient material and having an oval-shaped aperture in the center as well as a plurality of leg receiving holes, the catch being capable of releasing the protrusion of the needle part by widening the aperture when the legs of the pressing member are fully inserted into the leg receiving holes.

17. A syringe assembly according to claim 1, wherein the catch is rotatably fixed to the barrel at one end and capable of releasing the protrusion when the catch is pushed by the pressing member.

* * * * *